US006716895B1

(12) United States Patent
Terry

(10) Patent No.: US 6,716,895 B1
(45) Date of Patent: Apr. 6, 2004

(54) POLYMER COMPOSITIONS CONTAINING COLLOIDS OF SILVER SALTS

(75) Inventor: Richard N. Terry, Conyers, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/461,846

(22) Filed: Dec. 15, 1999

(51) Int. Cl.⁷ .......................... A61M 25/00; A61M 5/00; C08K 3/10
(52) U.S. Cl. ...................... 523/122; 524/403; 604/264; 604/265; 604/905
(58) Field of Search .......................... 523/122; 604/264, 604/265, 905; 524/403

(56) References Cited

U.S. PATENT DOCUMENTS

| | | |
|---|---|---|
| 861,231 A | 7/1907 | Clark |
| 1,557,234 A | 10/1925 | Bechhold |
| 1,557,235 A | 10/1925 | Bechhold |
| 1,642,089 A | 9/1927 | Schreier |
| 1,685,204 A | 9/1928 | Schreier |
| 1,691,755 A | 11/1928 | Buttner |
| 2,283,883 A | 5/1942 | Conconi |
| 2,363,354 A | 11/1944 | Peacock |
| 2,421,079 A | 5/1947 | Narcus |
| 2,459,896 A | 1/1949 | Schwarz |
| 2,459,897 A | 1/1949 | Schwarz |
| 2,562,488 A | 7/1951 | Fuchs |
| 2,602,757 A | 7/1952 | Kantrowitz, et al. |
| 2,639,997 A | 5/1953 | Drake |
| 2,653,893 A | 9/1953 | Romans |
| 2,689,191 A | 9/1954 | Pessel |
| 2,689,809 A | 9/1954 | Fessler |
| 2,702,253 A | 2/1955 | Bergström |
| 2,785,106 A | 3/1957 | Mendelsolm |
| 2,813,056 A | 11/1957 | Davis et al. |
| 2,813,059 A | 11/1957 | Davis et al. |
| 2,822,289 A | 2/1958 | Millard, Jr. |
| 2,879,175 A | 3/1959 | Umblia et al. |
| 2,947,282 A | 8/1960 | Brown |
| 3,092,552 A | 6/1963 | Romans .................. 167/72 |
| 3,184,376 A | 5/1965 | Degoli |
| 3,228,881 A | 1/1966 | Thomas |
| 3,300,336 A | 1/1967 | Gagliardi et al. |
| 3,380,848 A | 4/1968 | Horowitz |
| 3,396,727 A | 8/1968 | Mount |
| 3,404,028 A | 10/1968 | Trask et al. |
| 3,561,995 A | 2/1971 | Wu et al. |
| 3,566,874 A | 3/1971 | Shepherd |
| 3,591,329 A | 7/1971 | Chromeček et al. |
| 3,598,127 A | 8/1971 | Wepsic |
| 3,610,247 A | 10/1971 | Jackson |
| 3,639,575 A | 2/1972 | Schmolka |
| 3,695,921 A | 10/1972 | Shepherd et al. |
| 3,734,897 A | 5/1973 | Stoy et al. |
| 3,761,590 A | 9/1973 | Fox, Jr. |
| 3,822,238 A | 7/1974 | Blair et al. |
| 3,902,500 A | 9/1975 | Dryden |
| 3,953,545 A | 4/1976 | Stoy |
| 4,054,139 A | 10/1977 | Crossley .................. 128/260 |
| 4,076,622 A | 2/1978 | Costin |
| 4,197,220 A | 4/1980 | Rembaum et al. |
| 4,228,056 A | 10/1980 | Stoy |
| 4,248,444 A | 2/1981 | Bernstein et al. |
| 4,252,677 A | 2/1981 | Smith |
| 4,252,678 A | 2/1981 | Smith |
| 4,327,721 A | 5/1982 | Goldin et al. |
| 4,339,337 A | 7/1982 | Tricot et al. |
| 4,358,388 A | 11/1982 | Daniel et al. |
| 4,378,796 A | 4/1983 | Milhaud |
| 4,421,660 A | 12/1983 | Solc nee Hajna |
| 4,483,688 A | 1/1984 | Akiyama |
| 4,436,855 A | 3/1984 | Higgins et al. |
| 4,443,577 A | 4/1984 | Higgins et al. |
| 4,476,590 A | 10/1984 | Scales et al. .................. 3/1.91 |
| 4,479,795 A | 10/1984 | Mustacich et al. |
| 4,539,234 A | 9/1985 | Sakamoto et al. |
| 4,540,631 A | 9/1985 | Boultinghouse ............ 428/419 |
| 4,542,169 A | 9/1985 | Costerton |
| 4,563,184 A | 1/1986 | Korol |

(List continued on next page.)

FOREIGN PATENT DOCUMENTS

| | | |
|---|---|---|
| AU | 558588 | 2/1987 |
| CZ | 147057 | 3/1972 |
| DE | 3026258 A1 | 1/1982 |
| DE | 3228849 A1 | 2/1984 |
| DE | 3300203 A1 | 7/1984 |
| DE | 3302567 A1 | 7/1984 |
| DE | 89 15 538 | 12/1990 |
| DE | 3942112 A1 | 6/1991 |
| DE | 4115390 A1 | 4/1992 |
| DE | 4316920 A1 | 1/1994 |
| EP | 0038730 A1 | 10/1981 |

(List continued on next page.)

OTHER PUBLICATIONS

*Petrolite Corporation v. Watson*, Comr. Pats. (DC DC) 113 USPQ 248, 1957.*
*Austenal Laboratories, Incorporated v. Nobilium Processing* (DC NI11) 115 USPQ 44, 1957.*

(List continued on next page.)

Primary Examiner—Peter Szekely
(74) Attorney, Agent, or Firm—Kilpatrick Stockton LLP

(57) ABSTRACT

The present invention relates to antimicrobial compositions, methods for the production of these compositions, and use of these compositions with medical devices, such as catheters, and implants. The compositions of the present invention advantageously provide varying release kinetics for the active ions in the compositions due to the different water solubilities of the ions, allowing antimicrobial release profiles to be tailored for a given application and providing for sustained antimicrobial activity over time. More particularly, the invention relates to polymer compositions containing colloids comprised of salts of one or more oligodynamic metal, such as silver. The process of the invention includes mixing a solution of one or more oligodynamic metal salts with a polymer solution or dispersion and precipitating a colloid of the salts by addition of other salts to the solution which react with some or all of the first metal salts. The compositions can be incorporated into articles or can be employed as a coating on articles such as medical devices.

48 Claims, No Drawings

U.S. PATENT DOCUMENTS

| | | | |
|---|---|---|---|
| 4,563,485 A | 1/1986 | Fox, Jr. et al. | 523/113 |
| 4,564,361 A | 1/1986 | Akiyama | |
| 4,569,673 A | 2/1986 | Tesi | |
| 4,579,731 A | 4/1986 | Fox, Jr. et al. | |
| 4,581,028 A | 4/1986 | Fox, Jr. et al. | 623/2 |
| 4,592,920 A | 6/1986 | Murtfeldt | 427/2 |
| 4,603,152 A | 7/1986 | Laurin et al. | 604/265 |
| 4,612,337 A | 9/1986 | Fox, Jr. et al. | 523/113 |
| 4,615,705 A | 10/1986 | Scales et al. | 623/11 |
| 4,632,108 A | 12/1986 | Geil | |
| 4,642,104 A | 2/1987 | Sakamoto et al. | |
| 4,677,143 A | 6/1987 | Laurin et al. | 523/122 |
| 4,725,314 A | 2/1988 | Gulla et al. | |
| 4,728,323 A | 3/1988 | Matson | 604/304 |
| 4,734,097 A | 3/1988 | Tanabe et al. | |
| 4,738,782 A | 4/1988 | Yamauchi et al. | |
| 4,775,585 A | 10/1988 | Hagiwara et al. | |
| 4,810,582 A | 3/1989 | Gould et al. | |
| 4,820,292 A | 4/1989 | Korol et al. | |
| 4,847,049 A | 7/1989 | Yamamoto | |
| 4,849,223 A | 7/1989 | Pratt et al. | 424/409 |
| 4,871,790 A | 10/1989 | Lamanna et al. | |
| 4,902,503 A | 2/1990 | Umemura et al. | 424/83 |
| 4,906,466 A | 3/1990 | Edwards et al. | |
| 4,915,694 A | 4/1990 | Yamamoto et al. | |
| 4,923,450 A | 5/1990 | Maeda et al. | |
| 4,933,178 A | 6/1990 | Capelli | 424/78 |
| 4,948,739 A | 8/1990 | Charmot | |
| 4,950,256 A | 8/1990 | Luther et al. | |
| 4,952,411 A | 8/1990 | Fox, Jr. et al. | |
| 4,959,268 A | 9/1990 | Hagiwara et al. | |
| 4,973,320 A | 11/1990 | Brenner et al. | 604/265 |
| 4,981,886 A | 1/1991 | Nako et al. | |
| 4,999,210 A | 3/1991 | Solomon et al. | |
| 5,013,306 A | 5/1991 | Solomon et al. | |
| 5,019,096 A | 5/1991 | Fox, Jr. et al. | 623/1 |
| 5,037,395 A | 8/1991 | Spencer | |
| 5,049,140 A | 9/1991 | Brenner et al. | |
| 5,061,254 A | 10/1991 | Karakelle et al. | |
| 5,102,401 A | 4/1992 | Lambert et al. | 604/264 |
| 5,120,816 A | 6/1992 | Gould et al. | 528/76 |
| 5,146,916 A | 9/1992 | Catalani | |
| 5,180,585 A | 1/1993 | Jacobson et al. | 424/405 |
| 5,201,724 A | 4/1993 | Hukins et al. | |
| 5,290,585 A | 3/1994 | Elton | 427/2 |
| 5,320,908 A * | 6/1994 | Sodervall et al. | 428/461 |
| 5,322,520 A | 6/1994 | Milder | 604/265 |
| 5,322,887 A | 6/1994 | Howell et al. | |
| 5,326,567 A | 7/1994 | Capelli | 424/405 |
| 5,334,588 A | 8/1994 | Fox, Jr., deceased et al. | |
| 5,334,691 A | 8/1994 | Gould et al. | 528/76 |
| 5,357,636 A * | 10/1994 | Dresdner, Jr. et al. | 2/161.7 |
| 5,395,651 A | 3/1995 | Sodervall et al. | 427/304 |
| 5,413,788 A | 5/1995 | Edwards et al. | |
| 5,451,424 A | 9/1995 | Solomon et al. | 427/2.1 |
| 5,454,886 A | 10/1995 | Burrell et al. | |
| 5,478,563 A | 12/1995 | Erami | 424/409 |
| 5,492,763 A | 2/1996 | Barry et al. | 428/457 |
| 5,500,253 A | 3/1996 | Sanduja et al. | 427/385.5 |
| 5,503,840 A | 4/1996 | Jacobson et al. | 424/421 |
| 5,516,480 A | 5/1996 | Krall et al. | 264/343 |
| 5,520,664 A | 5/1996 | Bricault, Jr. et al. | 604/265 |
| 5,524,642 A | 6/1996 | Rosenblatt | |
| 5,567,495 A | 10/1996 | Modak et al. | |
| 5,595,750 A | 1/1997 | Jacobson et al. | 424/421 |
| 5,607,683 A | 3/1997 | Capelli | 424/405 |
| 5,616,338 A | 4/1997 | Fox, Jr. et al. | 424/423 |
| 5,662,913 A | 9/1997 | Capelli | 424/405 |
| 5,685,961 A | 11/1997 | Pourrezaei et al. | |
| 5,695,857 A | 12/1997 | Burrell et al. | |
| 5,708,023 A | 1/1998 | Modak et al. | |
| 5,709,672 A | 1/1998 | Illner | 604/265 |
| 5,709,870 A | 1/1998 | Yoshimura et al. | 424/404 |
| 5,725,510 A | 3/1998 | Hartmann et al. | |
| 5,736,591 A | 4/1998 | Dunn | 523/122 |
| 5,739,178 A | 4/1998 | Powell et al. | 523/122 |
| 5,744,151 A | 4/1998 | Capelli | 424/405 |
| 5,747,178 A | 5/1998 | Sodervall et al. | 428/624 |
| 5,762,638 A | 6/1998 | Shikani et al. | |
| 5,772,640 A | 6/1998 | Modak et al. | |
| 5,817,325 A | 10/1998 | Sawan et al. | 424/411 |
| 5,827,524 A | 10/1998 | Hagiwara et al. | 424/409 |
| 5,833,665 A | 11/1998 | Bootman et al. | 604/180 |
| 5,837,275 A | 11/1998 | Burrell et al. | |
| 5,848,995 A | 12/1998 | Walder | 604/265 |
| 5,849,311 A | 12/1998 | Sawan et al. | 424/406 |
| 5,958,440 A | 9/1999 | Burrell et al. | |
| 5,965,204 A | 10/1999 | Sodervall et al. | |
| 5,965,610 A | 10/1999 | Modak et al. | |
| 5,965,636 A | 10/1999 | Lark | |
| 5,976,562 A | 11/1999 | Krall et al. | |
| 5,985,308 A | 11/1999 | Burrell et al. | |
| 5,993,910 A | 11/1999 | Carre et al. | |
| 5,998,504 A | 12/1999 | Groth et al. | |
| 6,015,816 A * | 1/2000 | Kostyniak et al. | 514/299 |
| 6,017,553 A | 2/2000 | Burrell et al. | |
| 6,028,127 A | 2/2000 | Yanagase et al. | |
| 6,037,386 A | 3/2000 | Modak et al. | |
| 6,083,208 A | 7/2000 | Modak et al. | |
| 6,106,505 A | 8/2000 | Modak et al. | |
| 6,224,579 B1 | 5/2001 | Modak et al. | |
| 6,224,983 B1 | 5/2001 | Sodervall et al. | |
| 6,288,076 B1 * | 9/2001 | Kostyniak et al. | 514/299 |
| 2001/0010016 A1 | 7/2001 | Modak et al. | |

FOREIGN PATENT DOCUMENTS

| | | |
|---|---|---|
| EP | 0 206 024 A2 | 12/1986 |
| EP | 0229862 A2 | 7/1987 |
| EP | 0 301 717 A1 | 2/1989 |
| EP | 0 302 186 A2 | 2/1989 |
| EP | 0 318 258 A2 | 5/1989 |
| EP | 0399096 A2 | 11/1990 |
| EP | 0251783 B1 | 4/1993 |
| EP | 0328421 B1 | 4/1993 |
| EP | 0379269 B1 | 3/1994 |
| EP | 0 400 349 B1 | 2/1996 |
| EP | 0699081 B1 | 3/1999 |
| FR | 2109932 | 5/1972 |
| FR | 2330025 | 5/1977 |
| GB | 777679 | 6/1957 |
| JP | 59-218157 | 12/1984 |
| JP | 3-38504 | 2/1991 |
| JP | 03038504 A | 2/1991 |
| JP | 4272764 A | 9/1992 |
| JP | 4272765 A | 9/1992 |
| JP | 05117585 A | 5/1993 |
| JP | 5-117585 | 5/1993 |
| WO | WO 84/01721 A1 | 5/1984 |
| WO | WO 85/02190 A1 | 5/1985 |
| WO | WO 86/02006 A1 | 4/1986 |
| WO | WO 92/18098 A1 | 10/1992 |
| WO | WO 94/27652 A1 | 12/1994 |
| WO | WO97/31709 A1 | 9/1997 |

OTHER PUBLICATIONS

International Search Report from PCT patent application PCT/US00/42372.

Abstract of "Reaction of the bacterial load by the silver–coated endotracheal tube (SCET), a laboratory investigation" Hartmann et al, Technology and Healthcare 1999, 7 (5), p. 359–370, Dialog Access No. 10188995–20008765.

Maki et al., "An Attachable Silver Impregnated Cuff for Prevention of Infection With Central Venous Catheters: A Prospective Randomized Multicenter Trial," American Journal of Medicine, 1988, vol. 85, pp. 307–314.

Chemical Abstract No. 118:45828x, Koide et al.

Chemical Abstract No. 118:45828y, Koide et al.

Chemical Abstract No. 79:105832g, Stoy.

Chemical Abstract No. 88:51681x, Sulc et al.

ESP@cenet Abstract, DE3228849, Fraunhofer Ges Forschung, (Feb. 9, 1984).

ESP@cenet Abstract, DE3302567, Steidle Christoph, (Jul. 26, 1984).

ESP@cenet Abstract, DE3942112, Braun Melsungen AG, (Jun. 26, 1991).

ESP@cenet Abstract, DE4115390, Grosse Siestrup, (Apr. 30, 1992).

ESP@cenet Abstract, EP0302186, Carl Freudenberg, (Nov. 27, 1990).

Wrobleski, D. A. et al., "Surface Modification of Poly(ether urethane) by Chemical Infusion and Graft Polymerization", *Progress of Biomedical Polymers*, pp. 192–204, 1988. [Chemical Abstract No. 114:234998f, Wrobleski, et al.].

ESP@cenet Abstract, DE3300203, Zinon Douvlis, (Jul. 5, 1984).

* cited by examiner

US 6,716,895 B1

POLYMER COMPOSITIONS CONTAINING COLLOIDS OF SILVER SALTS

FIELD OF THE INVENTION

The present invention relates generally to polymer compositions and their use for making or coating articles, such as medical devices. More specifically the invention relates to antimicrobial compositions containing a polymer and oligodynamic salts.

BACKGROUND OF THE INVENTION

For many years silver and silver salts have been used as antimicrobial agents. An early medicinal use of silver was the application of aqueous silver nitrate solutions to prevent eye infection in newborn babies. Silver salts, colloids, and complexes have also been used to prevent and to control infection. For example, colloidal metallic silver has been used topically for conjunctivitis, urethritis, and vaginitis.

Other metals, such as gold, zinc, copper and cerium, have also been found to possess antimicrobial properties, both alone and in combination with silver. These and other metals have been shown to provide antimicrobial behavior even in minute quantities, a property referred to as "oligodynamic."

Additionally, silver is known for antimicrobial use with medical devices, such as catheters, cannulae, and stents. One conventional approach for obtaining antimicrobial medical devices is the deposition of metallic silver directly onto the surface of the substrate, for example, by vapor coating, sputter coating, or ion beam coating. However, these non-contact deposition coating techniques suffer many drawbacks. These drawbacks include poor adhesion, lack of coating uniformity, and the need for special processing conditions, such as preparation in darkness due to the light sensitivity of some silver salts. One particular drawback of these coatings is that the processes by which the coatings are formed do not adequately coat hidden or enclosed areas, such as the interior lumen of a catheter or stent. Additionally, these methods produce coatings that are very much like metallic silver in that they do not release silver from the coating and require contact with the coating to provide antimicrobial action. Though high concentrations of silver may be deposited on the substrate, very little free ionic silver is released on exposure to aqueous fluid. As a result, these coatings provide only limited antimicrobial activity. They essentially retard colonization of microbial agents on the surface of the device. However, because they do not release sufficient silver ions into aqueous fluids, they offer little or no protection from bacteria carried into the body upon insertion of the device and do not inhibit infection in the surrounding tissue.

Another method of coating silver onto a substrate involves deposition or electrodeposition of silver from solution. Drawbacks of these methods include poor adhesion, low silver pick-up on the substrate, the need for surface preparation, and high labor costs associated with multistep dipping operations usually required to produce the coatings. Adhesion problems have been addressed by inclusion of deposition agents and stabilizing agents, such as gold and platinum metals, or by forming chemical complexes between a silver compound and the substrate surface. However, inclusion of additional components increases the complexity and cost of producing such coatings.

With many medical devices, it is preferred to have a lubricious coating on the device. Lubricious coatings aid device insertion, reduce the trauma to tissue, and reduce the adhesion of bacteria. Another drawback to conventional methods which apply silver and other metals directly onto the surface of a medical device for which a lubricious coating is also desired is that a second, lubricious coating must be applied to the device over the antimicrobial coating, adding to manufacturing cost and time.

Some of these coatings release, to varying degrees, silver ions into the solution or tissue surrounding the substrate. However, activation of such coatings often requires conditions that are not suitable for use with medical implants, such as catheters, stents, and cannulae. These conditions include abrasion of the coating surface, heating to a temperature above 180° C., contact with hydrogen peroxide, and treatment with an electric current.

Another conventional approach for obtaining antimicrobial medical devices is the incorporation of silver, silver salts, and other antimicrobial compounds into the polymeric substrate material from which the article is formed. An oligodynamic metal may be physically incorporated into the polymeric substrate in a variety of ways. For example, a liquid solution of a silver salt may be dipped, sprayed or brushed onto the solid polymer, for example, in pellet form, prior to formation of the polymeric article. Alternatively, a solid form of the silver salt can be mixed with a finely divided or liquefied polymeric resin, which is then molded into the article. Further, the oligodynamic compound can be mixed with monomers of the material prior to polymerization.

There are several disadvantages to this approach. One such disadvantage is that larger quantities of the oligodynamic material are required to provide effective antimicrobial activity at the surface of the device. A second disadvantage is that it is difficult to produce articles that allow for the release of the oligodynamic material because most device polymers absorb little, if any, water to aid in the diffusion and release of the oligodynamic material, resulting in articles that provide only a limited antimicrobial effect.

Yet another approach for obtaining antimicrobial medical devices is the incorporation of oligodynamic agents into a polymeric coating which is then applied to the surface of the article. Typically, an oligodynamic agent is incorporated into the coating solution in the form of a solution or a suspension of particles of the oligodynamic agent. Problems associated with this approach include poor adhesion of the coating to the substrate, settling and agglomeration of the oligodynamic particles, and inadequate antimicrobial activity over time.

Settling of particles of the oligodynamic agent occurs as a result of the size and density of the particles. Settling of the particles from such solutions can cause unpredictable changes in the concentration of the oligodynamic agent in the composition. These changes in ion concentration result in several drawbacks to producing commercial products. First, unpredictable changes in the concentration of the oligodynamic agent make it difficult to produce a composition having a specific concentration of antimicrobial ions and, thus, a particular effectiveness. Additionally, these changes make it difficult to produce multiple batches of the composition having the same antibacterial concentration. Further, the concentration of the antimicrobial ions can affect other properties of the composition, such as its adhesive and lubricious properties. Consistency of antimicrobial activity is essential in the production of medical devices.

Another problem associated with particle suspensions is agglomeration of the particles. Particle agglomeration produces larger particle sizes which increases settling of particles from solution. Additionally, the agglomeration of particles in suspensions and coating solutions can produce particles in the coating that are large enough to be noticeable to the touch on the coated surface. Articles produced using such coatings have decreased patient comfort and, therefore, are undesirable.

Many researchers have attempted to overcome these problems. For example, U.S. Pat. No. 4,592,920 to Murtfeldt et al. discloses a process that attempts to overcome the settling and agglomeration problems in the art through the use of a comminuted metal having a particle size of 30 microns or less. The coating of the Muirtfeldt patent, however, exhibits several disadvantages. For example, the Murtfeldt coating exhibits poor adhesion which is overcome by the use of the following methods. First, the Murtfeldt patent recommends pretreatment of the catheter to leach undesirable compounds that interfere with the bonding of the coating to the surface of the catheter. Second, the Murtfeldt patent recommends the use of a bridging compound, or primer, to attach the coating to the surface of the catheter to increase adhesion. This adds an additional manufacturing step to the fabrication of a coated device. In addition to these disadvantages, it is likely that the process used to manufacture and coat the catheters in Murtfeldt will result in settling and agglomeration problems even with the use of silver having smaller particle sizes.

U.S. Pat. No. 4,849,223 to Pratt et al. attempts to overcome settling and agglomeration of the particles in his invention by using solutions that contain high concentrations of polymer or monomer solids and are, thus, viscous. Suspending particles in high viscosity coating solutions containing high polymer solids is a common method for reducing settling and agglomeration of the particles. The coatings made by this method are usually very thick and, as a result, are often not uniform. Thick coatings are also more costly, dry more slowly than thin coatings, and are more difficult to manufacture. The coatings of the Pratt patent also exhibit poor adhesion. To increase adhesion, the Pratt patent recommends using coating materials which are similar to the substrate to be coated, pretreating the surface of the substrate before the coating composition is applied, or applying an additional coating layer between the substrate and the coating.

U.S. Pat. No. 5,019,096 to Fox, Jr. et al. discloses a method for increasing the antibacterial activity of silver by incorporating a synergistic amount of chlorhexidine and a silver salt in a matrix-forming polymer. The polymer is such that it allows for release of the antimicrobial agent over an extended period of time. Fox, however, relies on dispersation of silver particles into coating solutions and will be susceptible to problems associated with particle settling and agglomeration.

U.S. Pat. No. 4,677,143 to Laurin et al. discloses a method to enhance release of the antimicrobial metal ions from the surface of a device by incorporating the antimicrobial metal into a binder having a low dielectric constant that coats or forms the device. The nature of the binder allows the particles to form chain-like structures among themselves. These chain-like structures allow the surface particles to dissolve to provide an initial dose of the antimicrobial agent and to create a pathway for interior particles to come to the surface to provide additional doses of the antimicrobial agent over time. Laurin, however, also relies on dispersation of silver particles into coating solutions and is susceptible to problems associated with particle settling and agglomeration.

U.S. Pat. No. 4,933,178 to Capelli discloses a polymer coating containing an oligodynamic metal salt of a sulfonylurea. The Capelli patent attempts to improve the solubility and stability of the antimicrobial metal in the coating and to provide for the sustained release of the antimicrobial agent by adding a carboxylic acid to the coating composition. The particular carboxylic acids and the proportions in which they are mixed determine the rate of release of the antimicrobial agent from the polymer coating composition.

U.S. Pat. No. 5,848,995 to Walder discloses the solid phase production of polymers containing AgCl as an antimicrobial agent. In the Walder process, solid polymer pellets are first soaked in a solution of silver nitrate which is absorbed into the pellets. The pellets are then rinsed, dried, and soaked in a solution of a sodium chloride. The chloride ions of the salt are absorbed into the polymer matrix of the pellets where they react with the silver nitrate to form silver chloride. The pellets are then rinsed, dried, and melt processed. The compositions of the Walder patent are limited to hydrophilic polymers, must be thermoformed, and do not contain other silver salts to provide multiple release rates, or other oligodynamic or medicinal agents to enhance antimicrobial effectiveness.

Therefore, there is a need in the art to provide a method for rendering articles, such as medical devices, resistant to infection, not only on the surface of the article but also in the surrounding tissue. There is also a need in the art for compositions which can be incorporated into articles to provide antimicrobial activity. Further, there is a need for compositions which can be employed as coatings for articles that exhibit improved adhesion. There is also a need for compositions that overcome the solubility, settling, and agglomeration problems of conventional oligodynamic compositions, and exhibit enhanced, sustained release of oligodynamic agents.

SUMMARY OF THE INVENTION

Stated generally, the present invention comprises antimicrobial compositions which in a first aspect provide the advantage of reduced settling and agglomeration by producing a minimal particle size of the oligodynamic salts in the compositions. The use of colloids in the compositions also permits incorporation of higher quantities of antimicrobial ions without the difficulties associated with the suspensions used in the prior art.

In another aspect, the compositions of the present invention provide the advantage of varying release kinetics for the active oligodynamic ions due to the different water solubilities of the different salts in the compositions. These varying release kinetics allow for an initial release of oligodynamic ions that provides antimicrobial activity immediately upon insertion, followed by a continual, extended release of the oligodynamic ions from the composition, resulting in sustained antimicrobial activity over time.

Stated somewhat more specifically, the present invention relates in one aspect to compositions that comprise a polymer and a colloid containing salts of one or more oligodynamic agents. In one disclosed embodiment, the polymer is a hydrophilic polymer. In another disclosed embodiment, the polymer is a hydrophobic polymer, while in yet another embodiment, the polymer is a combination of these two types of polymers.

In one disclosed embodiment, the invention comprises one or more salts of silver as the oligodynamic agent. In another embodiment, the composition optionally contains additional salts of other oligodynamic metals, such as zinc, gold, copper, cerium and the like. In yet another embodiment, the composition optionally comprises additional salts of one or more noble metals to promote galvanic action. In still another embodiment, the composition optionally comprises additional salts of platinum group metals such as platinum, palladium, rhodium, iridium, ruthenium, osmium, and the like. The compositions optionally contain any other components that provide beneficial properties to the composition or improve the antimicrobial effectiveness of the composition.

In a second aspect, the present invention relates to a process for producing these antimicrobial compositions. The process comprises the formation of colloids of oligodynamic agents in solutions, dispersions, or combinations of polymers solutions and dispersions. The terms "polymer composition" and "polymer solution" are used interchangeably throughout the specification and claims and both means any polymer solution, dispersion; or combination of polymer solutions and dispersions. The colloid can be formed first and then added to the polymer composition or can be formed in situ in the polymer composition. Preferably, the colloid is formed in situ in the polymer composition.

The process of forming the colloids comprises, for example, combining two or more salts, wherein at least one of the salts is the salt of an oligodynamic agent. These salts will be referred to herein as salt A and salt B. Salt A comprises one or more oligodynamic agents. Salt B comprises one or more salts that can react with salt A to form a colloid. Salts A and B can be combined in any amount and in any order. However, it is preferred that salt A be present in a stoichiometric amount or in excess when compared to salt B.

Optionally, additional components can be added to the antimicrobial compositions of the present invention. These components include, but are not limited to, additional oligodynamic agents, additional soluble salts, salts which provide galvanic action, and any other components which provide the compositions with beneficial properties or enhance the antimicrobial activity of the compositions. Such components include, but are not limited to, antimicrobial agents, antibiotics, and other medicinal agents.

In one disclosed embodiment, the antimicrobial composition of the invention is produced by forming a solution, dispersion, or combination of solutions and dispersions of one or more polymers. Next, a solution comprising salt A is added to the polymer composition. Then, a solution comprising salt B is added to the polymer composition to precipitate fine colloidal salt(s) of the oligodynamic agent(s). Where the oligodynamic agent is a metal salt, the metal cation of salt A reacts with the anion of salt B to form a less soluble salt which precipitates as a fine colloid. Salt B is added to the polymer composition in an amount sufficient to react with some or all of salt A. Optionally, other salts are then added in amounts to react with some or all of the remaining amount of salt A.

In another disclosed embodiment, salt B is added to the polymer composition, followed by the addition of an excess or stoichiometric amount of salt A. In yet another embodiment, salts A and B can be combined to form a colloid which is then added to the polymer composition.

The final polymer composition formed by these processes contains one or more colloidal salts, composed of the oligodynamic cations of salt A and the anions of salt B, and one or more soluble salts, composed of the anions of salt A and the cations of salt B.

In another aspect, the present invention relates to an article of, manufacture which comprises a substrate and the antimicrobial compositions of the present invention. In a disclosed embodiment, the composition is employed in the manufacture of the article itself. Thus, the final article is composed of one or more of the compositions of the present invention, alone or in admixture with other polymeric components. In another disclosed embodiment, the composition is applied to a preformed article as a coating. The coated article may be produced, for example, by dipping the article into the composition or by spraying the article with the composition and then drying the coated article. In a preferred embodiment, the compositions are used to coat medical devices.

DETAILED DESCRIPTION OF THE PREFERRED EMBODIMENTS

The Composition

In a first aspect, the present invention provides antimicrobial compositions. The compositions comprise a polymer and a colloid comprised of the salts of one or more oligodynamic agents. The term "oligodynamic agents" as used in the present invention refers to any compound that can provide antimicrobial activity, even when present in small quantities.

Any polymer may be employed in the present invention, including hydrophilic polymers, hydrophobic polymers, and mixtures of these two types of polymers. The use of hydrophilic polymers is preferred because such polymers have additional benefits. These benefits include increased lubricity for patient comfort, increased absorption of aqueous fluids from the body which aids in the release of oligodynamic ions from the composition, inhibition of bacterial attachment, and improved solubility for some metal salts. Hydrophilic polymers best suited to the invention are those that are soluble in water or in organic solvents containing water. The ability to add water to the polymer composition without precipitating the polymer allows the addition of water-soluble salts directly to the coating composition. Water facilitates the formation of salt colloids within the polymer composition. For this reason, it is preferred that the polymer solution contain from 1 to 50% water by weight, more preferably from 5 to 30% water.

However, the use of water is not limiting, as salt colloids can also be formed using alcohols, organic solvents, or both that contain little or no water. The use of alcohols and organic solvents, containing from 0 to 1% water are preferred when hydrophobic polymers are employed in the present invention.

Examples of hydrophilic polymers which may be used to form the compositions include, but are not limited to, polyurethanes, including polyether polyurethanes, polyester polyurethanes, polyurethaneureas, and their copolymers; polyvinylpyrrolidones; polyvinyl alcohols; polyethylene glycols and their copolymers; polypropylene glycols and their copolymers; polyoxyethylenes and their copolymers; polyacrylic acid; polyacrylamide; carboxymethyl cellulose; cellulose and its derivatives; dextrans and other polysaccharides; starches; guar; xantham and other gums and thickeners; collagen; gelatins; and other biological polymers. Preferred hydrophilic polymers are polyurethanes and polyurethane copolymers, such as polyether polyurethaneurea.

Examples of hydrophobic polymers best suited for use in the present invention include, but are not limited to, polytetrafluoroethylene, polyvinyl chloride (PVC), polyvinylacetate, poly(ethylene terephthalate), silicone, polyesters, polyamides, polyureas, styrene-block copolymers, polymethyl methacrylate, acrylic-butadiene-styrene copolymers, polyethylene, polystyrene, polypropylene, natural and synthetic rubbers, acrylonitrile rubber, and mixtures and copolymers of any of the above. The preferred hydrophobic polymer depends upon the substrate to be coated. Hydrophobic polymers that are chemically similar or identical to the substrate are advantageously used alone or in combination with hydrophilic polymers to form coatings that enhance adhesion of the coating to the substrate.

The colloid of the present invention comprises one or more oligodynamic salts. In the discussion of the process below, these salts are referred to as salt A. In a preferred embodiment, the oligodynamic salts comprise one or more salts of oligodynamic metals. The salts may be different salts of the same oligodynamic metal or may be salts of different oligodynamic metals. Oligodynamic metals useful in the present invention include, but are not limited to, silver, platinum, gold, zinc, copper, cerium, gallium, osmium, and the like. The preferred oligodynamic metal is silver.

Salts of other metals may be employed to form the colloid. In the discussion of the process below, these salts are referred to as salt B. These salts contain cationic ions that include, but are not limited to, calcium, sodium, lithium, aluminum, magnesium, potassium, manganese, and the like, and may also include oligodynamic metal cations such as copper, zinc, and the like. These salts contain anions that include, but are not limited to, acetates, ascorbates, benzoates, bitartrates; bromides, carbonates, chlorides, citrates, folates, gluconates, iodates, iodides, lactates, laurates, oxalates, palmitates, perborates, phenosulfonates, phosphates, propionates, salicylates, stearates, succinates, sulfadiazines, sulfates, sulfides, sulfonates, tartrates, thiocyanates, thioglycolates, thiosulfates, and the like. The invention may also be practiced with oxides serving as Salt B, including, but not limited to, oxides of calcium, sodium, lithium, aluminum, magnesium, potassium, manganese, and the like, and may also include oxides of oligodynamic metals such as copper, zinc, and the like.

The compositions of the present invention can also contain additional antimicrobial materials. For example, the compositions can contain salts of metals that enhance the antimicrobial effect of the oligodynamic metal, such as the platinum group metals, or other metals that promote galvanic action.

The compositions of the present invention can also contain any combination of additional medicinal compounds. Such medicinal compounds include, but are not limited to, antimicrobials, antibiotics, antifungal agents, antiviral agents, antithrombogenic agents, anesthetics, antiinflammatory agents, analgesics, anticancer agents, vasodilation substances, wound healing agents, angiogenic agents, angiostatic agents, immune boosting agents, growth factors, and other biological agents. Suitable antimicrobial agents include, but are not limited to, biguanide compounds, such as chlorhexidine and its salts; triclosan; penicillins; tetracyclines; aminoglycosides, such as gentamicin and Tobramycin™; polymyxins; rifampicins; bacitracins; erythromycins; vancomycins; neomycins; chloramphenicols; miconazole; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity.

The compositions can also contain auxiliary components. Examples of such auxiliary components include, but are not limited to, viscosity and flow control agents, antioxidants, conventional pigments, air release agents or defoamers, and discolorants. The composition may also contain conventional dyes and pigments to impart color or radiopacity or to enhance the aesthetic appearance of the compositions. The compositions can also contain additional lubricating agents and other additives that enhance patient comfort and tissue health.

While not wishing to be bound by the following mechanism, it is believed that many of the advantageous properties of the present compositions result from the differences in the solubility of the different metal salts present in the colloid. These differing solubilities of the metal salts in the colloid provide varying release kinetics for the active oligodynamic metal(s). For example, with a medical device composed of, or coated with, the compositions of the present invention, those salts that have high water solubility will be released from the coating rather quickly, providing a high initial dose of antimicrobial activity to kill bacteria introduced upon insertion of the device in the patient. This initial dose is sometimes referred to as "quick kill," and this antimicrobial activity is identified by the ability of a coated device or composition to create zones of no bacterial growth around the device or composition when it is placed in a bacterial culture. This test is known as a "zone of inhibition" assay. Those salts having lower water solubilities will be released more slowly from the composition, resulting in a sustained or extended antimicrobial activity over time.

Selection of salts having varying degrees of solubility in the composition allows tailoring of the composition to the specific application of the article comprising the composition. Specifically, compositions of the invention can be tailored to kill bacteria introduced during the insertion of a medical device, both on the surface of the device and in the surrounding fluid and tissue, by both the quick release of antimicrobial metal salts, followed by prolonged inhibition of bacterial migration and growth by the slower release of less soluble antimicrobial metal salts over an extended period of time. The ability to tailor the release of the oligodynamic agent is advantageous over conventional antimicrobial compositions, as it provides for both immediate and sustained antimicrobial activity.

Another advantage of the compositions of the present invention is that the formation of colloids within the polymer composition produces ultra-fine particles that possess a minimal particle size for the metal salts. This minimal particle size retards settling and agglomeration. The use of colloids in the composition also permits incorporation of higher quantities of antimicrobial metal without the difficulties associated with the suspensions used in the prior art.

By reducing or eliminating the problems associated with conventional antimicrobial polymer compositions, the present invention provides reproducible compositions having a specific antimicrobial ion concentration with a specific antimicrobial ion release profile that can be tailored through the specific salt combinations selected to provide optimum antibiotic activity over an extended period of time. For example, compositions of the invention can be tailored to release the bulk of their oligodynamic agents within 5 days for a medical device with a short term use in the body, such as a wound drain, or within 30 days for a device with a longer term use such as a foley catheter.

The tailored delivery embodiment of the invention will now be further described in terms of a polyurethane composition containing a colloid of specific silver salts. It is to be understood that this is simply an example of one embodiment of the invention and that one of skill in the art, based upon the present disclosure, could pick and choose salts having differing solubilities to provide a composition having a suitable release profile for a particular purpose.

A coating solution is formed from a 4.7% solution of a polyether polyurethane-urea block copolymer in a mixture of THF/alcohol in a 75/25 ratio by weight. A sufficient quantity of 10% silver nitrate (AgNO$_3$) solution in water is added to the TPH copolymer solution to produce a final silver concentration of approximately 15%, based on the weight of coating solids in the solution.

Aqueous solutions of sodium chloride, zinc iodide, sodium citrate, sodium acetate, and sodium lactate (each 1.0% solutions) are added to the copolymer solution in sufficient amounts for each salt to react with 15% of the silver nitrate present in the composition. Colloids of silver chloride, silver iodide, silver citrate, silver acetate, and silver lactate are formed in the final coating composition. The coating composition also contains 25% unreacted soluble silver nitrate, as well as the silver nitrate and zinc nitrate salt products. The differences in the solubility of the different salts in the composition will result in different and prolonged rates of release of the oligodynamic silver in the coating composition when a device coated with the composition is exposed to body fluid.

Silver nitrate is the most soluble of the salts present in the composition and will be released rapidly upon initial exposure of the coating to body fluid. Silver lactate, which has a lower solubility than silver nitrate but a higher solubility than the other salts present, will be released next. Then, the silver acetate, followed by the silver citrate, and then the silver chloride, and, lastly, the silver iodide will be released from the coating composition based upon their relative solubilities.

The initial release and the duration of release of the oligodynamic agents from the composition depends upon several factors. These factors include the relative water solubilities of the particular salts formed in the colloid and the concentration of the salts in the colloid. This release can range, for example, from a few days to several months, and can be tailored through the choice and number of salts formed in the composition for the intended purpose of the device to be coated.

The compositions of the invention can also be tailored to provide other desired properties, such as surface lubricity. Further, the compositions may contain other medicinal or otherwise beneficial agents.

Process for Preparing the Composition

In a second aspect, the present invention relates to a process for producing the compositions of the invention. In general terms, the process comprises the formation of colloids of oligodynamic agents in polymer solutions. The colloid can be formed first and then added to the polymer composition or can be formed in situ in the polymer composition. Preferably, the colloid is formed in situ in the polymer composition.

The process of forming the colloids comprises, for example, combining two or more salts, wherein at least one of the salts is the salt of an oligodynamic agent. These salts will be referred to as salt A and salt B. Salt A comprises one or more oligodynamic agents. Salt B comprises one or more salts that can react with salt A to form a colloid. Salts A and B can be combined in any amount and in any order. However, it is preferred that salt A be present in a stoichiometric amount or in excess when compared to salt B.

Optionally, additional components can be added to the compositions. These components include, but are not limited to, additional oligodynamic agents, additional soluble salts, salts which provide galvanic action, and any other components which provide the compositions with beneficial properties or enhance the antimicrobial activity of the compositions. Such components include, but are not limited to, antimicrobial agents, antibiotics, and other medicinal agents.

In one disclosed embodiment, the composition is produced by forming a solution, dispersion, or combination of solutions and suspensions of one or more polymers. Next, a solution comprising salt A is added to the polymer composition. Then, a solution comprising salt B is added to the polymer composition to precipitate fine colloidal salt(s) of the oligodynamic agent(s) of salt A. Where the oligodynamic agent is a metal salt, the metal cation of salt A reacts with the anion of salt B. Salt B is added to the polymer composition in an amount sufficient to react with some or all of salt A. Optionally, other salts are then added in amounts to react with some or all of the remaining amount of salt A.

In another disclosed embodiment, salt B is added to the polymer composition, followed by the addition of an excess or stoichiometric amount of salt A. In yet another embodiment, salts A and B can be combined to form a colloid which is then added to the polymer composition.

The final polymer composition formed by these processes contains one or more colloidal salts, composed of the oligodynamic cations of salt A and the anions of salt B, and one or more soluble salts, composed of the anions of salt A and the cations of salt B. Additionally, other salts may be added to the composition that do not react in solution but provide some beneficial effect such as stabilization of the colloid, modification of antimicrobial ion release rate, promotion of galvanic action, increase in antimicrobial effectiveness, or enhancement of biocompatibility. Further, other compounds may be added to the composition, including, but not limited to, medicinal agents, lubricants, nutritional agents, antioxidants, dyes and pigments, and other additives.

As noted above, any polymer can be used to form the compositions of the present invention. When hydrophilic polymers are used, it is preferable that the polymers be soluble in water or in organic solvents containing some water. The ability to add water to the polymer composition without precipitating the polymer allows the addition of water-soluble salts directly to the coating composition. The use of water in the polymer composition increases the solubility of the salts, resulting in the formation of finer more stable colloids. However, it takes longer for the coating compositions to dry when the water content is very high. For this reason, the preferred amount of water in the hydrophilic polymer compositions is about 50% or less. Such concentrations provide for faster drying times while maintaining the beneficial properties provided by the water in the composition.

In contrast, when hydrophobic polymers are used either alone or in combination with hydrophilic polymers, it is desirable to limit the amount of water present in the composition to avoid precipitation of the hydrophobic polymer with the colloid. In such instances the amount of water present in the polymer composition is preferably 1% or less. While it is possible to practice the invention in the absence of water in the composition, it is preferable to have some water present. Thus, when hydrophobic polymers are employed in the present invention, the preferred water content of the polymer compositions is between about 0.1% and 1% by weight. It is advantageous to employ salts that are soluble in alcohols or organic solvents when hydrophobic polymers employed.

Examples of water-soluble silver salts suitable for use in the present invention include, but are not limited to, silver nitrate, silver acetate and silver lactate. Examples of salts which are soluble in alcohols and organic solvents include, but are not limited to, silver nitrate, sodium iodide, sodium lactate, sodium propionate, sodium salicylate, zinc chloride, zinc acetate, zinc salicylate, gold trichloride, gold tribromide, palladium chloride and hydrogen-hexachloroplatinate.

Examples of alcohols that are useful in the present invention include, but are not limited to, methanol, ethanol, propanol, isopropanol, and butanol. Examples of organic solvents that can be used to form solutions of the oligodynamic salts include, but are not limited to, acetone, tetrahydrofuran (THF), dimethylformamide (DMF), dimethylsulfoxide (DMSO), and acetonitrile. These organic solvents are especially useful when they contain a small amount of water.

It is also possible to prepare polymer compositions from supercritical fluids. The most common of these fluids is liquefied carbon dioxide.

In a preferred embodiment, the polymer composition in which the colloid is formed is a hydrophilic polyether polyurethaneurea. This polymer is a substantially noncovalently crosslinked reaction product of one or more diols, water and an organic diisocyanate. The urea segments of the polymer provide improved strength, increased viscoelasticity, and decreased water absorption. These polymers typically absorb water in amounts from 50 to 100% their weight while remaining strong and elastic.

Diols useful in the formation of these polymers include, but are not limited to, medium and long chain poly (oxyethylene) glycols having a number average molecular weights between 250 and 20,000. Example of such diols are "Carbowax" compounds sold by Union Carbide.

Organic diisocyanates useful to form these polymers include, but are not limited to, tetramethylene diisocyanate, hexamethylene diisocyanate, trimethylhexamethylene diisocyanate, dimer acid diisocyanate, isophorone diisocyanate, diethylbenzene diisocyanate, decamethylene 1,10-diisocyanate, cyclohexylene 1,2-diisocyanate, cyclohexylene 1,4-diisocyanate, methylene bis(cyclohexyl-4-isocyanate), 2,4- and 2,6-tolylene diisocyanate, 4,4'-diphenylmethane diisocyanate, 1,5-naphthaliene diisocyanate, dianisidine diisocyanate, tolidine diisocyanate, xylylene diisocyanate, and tetrahydronaphthalene-1,5-diisocyanate.

In another preferred embodiment, the polymer coating composition comprises a combination of a hydrophilic polyurethane, a polymer that is similar or identical to the polymer substrate to be coated, and, optionally, other polymers which aid coating adhesion and physical properties. Antimicrobial salt colloids are prepared in this composition as disclosed previously, with the exception that, depending on the second polymer used, some or all of the water used to prepare salt solutions can be replaced with alcohols or other organic solvents to prevent precipitation of the second polymer. Another exception is that the salts elected must be soluble in solvents compatible with those in which the polymers are soluble. As an example of this preferred embodiment, a solution of a hydrophilic polyether polyurethaneurea in THF can be combined with a solution of polyvinyl chloride (PVC) in methylene chloride in equal amounts. Then, silver nitrate can be dissolved in ethanol and added to the solution without precipitation. Ethanol is used to dissolve the silver nitrate instead of water because PVC has a tendency to precipitate when water is added to the solution. Finally, a dilute solution of zinc chloride in ethanol/water can be slowly added to the polymer composition to produce a fine silver chloride colloid without precipitation of the PVC. The final concentration of water in the coating is less than 1%. The coating solution is then used to dip-coat PVC catheters. The finished coating is well adhered, durable, lubricious when wetted, and contains colloidal antimicrobial salts.

In another embodiment, the polymer composition comprises a hydrophilic polymer as defined in commonly owned U.S. Pat. No. 6,329,428, filed Nov. 10, 1998, herein incorporated by reference. In general, the polymer is a polyurethane-urea-silane copolymer prepared from the following ingredients: (1) one or more polyisocyanate, (2) one or more lubricious polymer having at least two functional groups, which may be the same or different and are reactive with an isocyanate functional group, and (3) one or more organo-functional silanes having at least two functional groups, which may be the same or different and are reactive with an isocyanate functional group and with a silicone rubber substrate. While these copolymers may be prepared in a variety of ways, preferably they may be prepared by first forming a prepolymer from the polyisocyanate(s) and lubricious polymer(s) followed by reaction with the organo-functional silane(s). A catalyst is optionally employed during reaction of the isocyanate with the polyol.

Isocyanates useful to form these polymers include, but are not limited to, 4,4'-diphenylmethane diisocyanate and position isomers thereof, 2,4- and 2,6-toluene diisocyanate (TDI) and position isomers thereof, 3,4-dichlorophenyl diisocyanate, dicyclohexylmethane-4,4'-diisocyanate (HMDI), 4,4'-diphenylmethane diisocyanate (MDI), 1,6-hexamethylene diisocyanate (HDI) and position isomers thereof, isophorone diisocyanate (IPDI), and adducts of diisocyanates, such as the adduct of trimethylolpropane and diphenylmethane diisocyanate or toluene diisocyanate.

Polyols useful to form these polymers include, but are not limited to, polyethylene glycols, polyester polyols, polyether polyols, caster oil polyols, and polyacrylate polyols, including Desmophen A450, Desmophen A365, and Desmophen A160 (available from Mobay Corporation), poly(ethylene adipates), poly(diethyleneglycol adipates), polycaprolactone diols, polycaprolactone-polyadipate copolymer diols, poly (ethylene-terephthalate)diols, polycarbonate diols, polytetramethylene ether glycol, ethylene oxide adducts of poly-oxypropylene diols, and ethylene oxide adducts of polyoxypropylene triols.

Catalysts useful to form these polymers include, but are not limited to, tertiary amines, such as N,N-dimethylaminoethanol, N,N-dimethyl-cyclohexamine-bis (2-dimethyl aminoethyl)ether, N-ethylmorpholine, N,N,N', N',N',N"-pentamethyl-diethylene-triamine, and 1-2 (hydroxypropyl)imidazole, and metallic catalysts, such as tin, stannous octoate, dibutyl tin dilaurate, dioctyl tin dilaurate, dibutyl tin mercaptide, ferric acetylacetonate, lead octoate, and dibutyl tin diricinoleate.

Silanes useful to form these polymers include, but are not limited to, N-beta-(aminoethyl)-gamma-aminopropyl-trimethoxy silane and diamino-alkoxysilanes, such as N-(2-amninoethyl)-3-aminopropylmethyl-dimethoxy silane.

These polymers preferably have from 7 to 12% by weight silane based upon the weight of the entire polymer. The preferred ratio of isocyanate functional groups to alcohol or other isocyanate reactive functional groups is from 1.1:1 to 2:1. Viscosity of the polymer solution is a function of molecular weight of the polymer and the solids content of the solution and is controlled by addition of solvent to the solution. The preferred copolymer solution for dip coating has a kinematic viscosity in the range of about 1.5 cS to about 20 cS (centistokes), and a solids content in a range of about 0.4 to about 5.

In yet another embodiment, the polymer composition comprises a solution of a hydrophilic polymer as defined in U.S. Pat. No. 5,290,585, which is hereby incorporated by reference. The polymer is a polyurethane-polyvinyl pyrrolidone prepared by mixing the appropriate amounts of isocyanate, polyol, and polyvinyl pyrrolidone (PVP) stock solution. Additional solvents can be added to adjust the viscosity and solids content. Solids content may be in the range of 0.4 to 15% by weight, depending on the solvent used and other considerations. The stoichiometric ratio of total NCO groups in the isocyanate to total OH groups in the polyol may vary from 0.75 to 3.0. Preferably, the isocyanate has at least two NCO groups per molecule and the polyol has at least two OH groups per molecule. The ratio of polyurethane formed in situ to PVP ranges from 0.05 to 3.0 by weight.

The PVP employed to form these polymers preferably has a mean molecular weight from about 50,000 to 2.5 million Daltons. Specific preferred PVP polymers are Kollidon 90, Luviskol K90, Luviskol K80, and Luviskol K60, all available from BASF Corp. (Parsippany, N.J.) and Plasdone 90, PVP K90, and PVP K120, all available from GAF Corporation.

Isocyanates suitable to form these polymers include, but are not limited to, polymethylenepolyphenyl isocyanate, 4,4'-diphenylmethane diisocyanate and position isomers thereof, 2,4-tolylene diisocyanate and position isomers thereof, 3,4-dichlorophenyl diisocyanate, isophorone isocyanate, and adducts or prepolymers of isocyanates, such as the isocyanate prepolymer available as Vorite 63 from CasChem, Inc. (Bayonne, N.J.). Other examples of polyisocyanates useful in the present invention are those listed in ICI Polyurethanes Book, by George Woods, published by John Wiley and Sons, New York, N.Y. (1987).

Polyols useful to form these polymers include, but are not limited to, polyester polyols, polyether polyols, modified polyether polyols, polyester ether polyols, caster oil polyols, and polyacrylate polyols, including Desmophen A450, Desmophen A365, and Desmophen A160 available from Mobay Corporation (Pittsburgh, Pa.). Preferred polyols include caster oil and caster oil derivatives, such as DB oil, Polycin-12, Polycin 55, and Polycin 99F available from CasChem, Inc. Preferred diols include, but are not limited to, Desmophen 651A-65, Desmophen 1300-75, Desmophen 800, Desmophen-550 DU, Desmophen-1600U, Desmophen-1920D, and Desmophen-1150, available from Mobay Corporation, and Niax E-59 and others available from Union Carbide (Danbury, Conn.).

Suitable solvents for use in the formation of these polymers are those which are capable of dissolving the isocyanate, the polyol, and the polyvinyl pyrrolidone without reacting with any of these components. Preferred solvents include, but are not limited to, methylene chloride, dibromomethane, chloroform, dichloroethane, and dichloroethylene.

When a composition containing this polymeric solution is to be used as a coating, the coating is cured, after application to the substrate, at a temperature in the range of approximately 75° F. to approximately 350° F. for a period in the range of about 2 minutes to about 72 hours.

The process of the invention will now be further described in terms of the formation of a colloid of silver chloride from silver nitrate and sodium chloride in a polyurethane polymer coating solution. It is to be understood that this is simply an example of one preferred embodiment of the invention and that any polymer or combination of polymers and any mixture of salts that will form a colloid within the polymer solution can be employed in the present invention.

First, a 4.7% solution of a polyether polyurethane-urea block copolymer is prepared in a mixture of THF/ethanol in a 75/25 ratio by weight. A sufficient quantity of 10% silver nitrate ($AgNO_3$) solution in water is added to the TPH copolymer solution to produce a final silver concentration of approximately 15%, based on coating solids in the solution. An aqueous solution of 1.0% sodium chloride (NaCl) is then slowly added to the solution with stirring in an amount sufficient to react with 50% of the $AgNO_3$. The NaCl reacts with the $AgNO_3$ to produce a colloidal suspension of the poorly water soluble salt, AgCl, and the soluble salt, $NaNO_3$, from half of the $AgNO_3$. The amount of water in the final coating solution is about 30% of the total solvent weight. The final polymer concentration in the coating solution is 3.3%, based upon solvent and polymer weights.

A 16 Fr latex Foley catheter can then be coated with the composition by dipping it into the composition solution, withdrawing it at a controlled rate and drying it using standard methods. The finished coating contains both the water soluble, and therefore fast releasing, $AgNO_3$, and the water insoluble, and therefore slow releasing, AgCl.

Uses of the Composition

In a third aspect, the present invention relates to an article of manufacture. In a preferred embodiment, the antimicrobial composition can be used as a coating on a preformed article to provide antimicrobial activity to the surface of the article and to the environment surrounding the article through the continual release of oligodynamic ions. Any article can be coated with the antimicrobial compositions of the present invention. The composition is particularly suited for the production of medical devices, which include, but are not limited to, catheters, cannulae, stents, guide wires, implant devices, contact lenses, IUDs, peristaltic pump chambers, endotracheal tubes, gastroenteric feeding tubes, arteriovenous shunts, condoms, oxygenator and kidney membranes, gloves, pacemaker leads, and wound dressings.

In a second embodiment, the antimicrobial composition can be prepared as a high solids solution and used alone or mixed with other polymers to form the article itself. Polymers which are useful to form the articles of the invention include, but are not limited to, natural and synthetic rubber, especially latex rubber, acrylonitrile rubber, PVC plastisol, PVC, polyurethanes, silicone, polycarbonates, acrylates, poly amides, polypropylenes, polyethylenes, polytetrafluoroethylenes, polyvinylacetate, poly(ethylene terephthalate), polyesters, polyamides, polyureas, styrene-block copolymers, polymethyl methacrylate, acrylic-butadiene-styrene copolymers, polystyrene, cellulose, and derivatives and copolymers of any of the above.

As nonlimiting examples, compositions of the invention can be admixed into latex rubber for fabrication of catheters, gloves, and other dipped latex products by standard form dipping methods, and vinyl plastisols can be mixed with compositions of the invention to provide dippable and castable antimicrobial PVC devices. Thus, the final article can be composed of one or more of the compositions of the present invention in admixture with other polymeric components.

Alternatively, compositions of the invention can be formulated into high solids coating compositions that can be used to dip-fabricate a variety of medical devices, such as catheters, stents, gloves, condoms, and the like.

By another method, compositions of the invention can be dried and melt processed, for example, by injection molding and extrusion. Compositions used for this method can be used alone or compounded with any other melt-processable material for molding and extrusion of antimicrobial articles.

The antimicrobial compositions of the invention are preferably coated onto preformed articles. When used as a coating, the compositions can be applied by any means, including those methods known in the art. For example, the compositions can be brushed or sprayed onto the article, or the article can be dipped into the composition. For example, the article can be dipped into the antimicrobial polymer solution at a rate of about 10–80 inches per minute (ipm), preferably about 40 ipm. The article is allowed to remain in the antimicrobial polymer solution for a period of about 0–30 seconds, preferably about 5–15 seconds. The article is then withdrawn at a rate of about 10–80 ipm, preferably about 15–30 ipm. Once the article has been coated with the copolymer of the invention, it is allowed to air dry for a period of at least about 10 minutes before drying is completed in is an oven for a period of about 5–60 minutes at a temperature in the range of about 40–100° C. Preferably, oven drying occurs for a period of about 15 minutes at a temperature of about 50° C. The coated article can optionally be dried with a hot air stream at a temperature in the range of approximately 40° C. to approximately 100° C. for a period of about 5–60 minutes to remove residual solvent.

This invention is further illustrated by the following examples, which are not to be construed in any way as imposing imitations upon the scope of the invention.

EXAMPLES

Example 1

To form the coating solution, a 4.7% solution of a polyether polyurethane-urea block copolymer manufactured by Tyndale Plains-Hunter Ltd. (TPH) was prepared in a mixture of THF/alcohol in a 75/25 ratio by weight. A sufficient quantity of 10% silver nitrate ($AgNO_3$) solution in water was added to the TPH copolymer solution to produce a final silver concentration of approximately 15%, based on the weight of coating solids in the solution. An aqueous solution of 1.0% sodium chloride (NaCi) was added to the solution in an amount sufficient to react with 50% of the $AgNO_3$ to produce a colloid of the poorly water soluble salt, AgCl, from half of the $AgNO_3$ in the coating solution. The NaCl solution was added slowly to the polymer solution and the solution began to turn cloudy with the formation of the fine colloidal AgCl. The amount of water in the final coating solution was about 30% of the total solvent weight. The final polymer concentration in the coating solution was 3.3%, based upon solvent and polymer weights.

A 16 Fr latex Foley catheter was then coated by dipping it into the coating solution, withdrawing it at a controlled rate to control the thickness of the coating and drying the catheter coating using standard methods. The finished coating contained both the water soluble, and therefore fast releasing, $AgNO_3$ and the water insoluble, and therefore slow releasing, AgCl.

Example 2

The process of Example 1 was repeated, except that a 1.0% solution of zinc chloride was used in place of the 1.0% solution of sodium chloride, resulting in the formation of a silver chloride colloid and zinc nitrate from half the silver nitrate in the coating solution. Zinc chloride was added in an amount of one half the amount of NaCl added in Example 1 because one mole of zinc chloride reacts with 2 moles of silver nitrate.

Example 3

The process of Example 1 was repeated, except that a 1.0% solution of copper chloride was used in place of the 1.0% solution of sodium chloride, resulting in the formation of a silver chloride colloid and copper nitrate from half the silver nitrate in the coating solution. Copper chloride was added in an amount of one half the amount of NaCl added in Example 1 because one mole of copper chloride reacts with 2 moles of silver nitrate.

Example 4

The process of Example 1 was repeated, except that the 1.0% solution of sodium chloride was replaced with a 1.0% solution of sodium iodide, resulting in the formation of a silver iodide colloid and sodium nitrate from half the silver nitrate in the coating solution. Silver iodide is a local antiinfective agent and has a lower water solubility than silver chloride, providing a slower releasing silver salt than silver chloride.

Example 5

The process of Example 1 was repeated, except that the 1.0% solution of sodium chloride was replaced with a 1.0% solution sodium propionate, resulting in the formation of a silver propionate colloid and soluble sodium nitrate, along with the remaining silver nitrate in the solution. Silver propionate is a local antiinfective and is more water soluble than AgCl or AgI, providing a faster releasing salt than silver chloride or silver iodide.

Example 6

The process of Example 1 was repeated, except that the 1.0% solution of sodium chloride was replaced with a 1.0% solution of sodium lactate, resulting the formation of a silver lactate colloid and sodium nitrate, along with the remaining silver nitrate in the coating solution. Silver lactate is a local antiinfective and is more water soluble than sodium propionate, AgCl or AgI, providing one of the fastest releasing silver salts, other than the soluble silver nitrate.

Example 7

The process of Example 1 was repeated, except that the 1.0% solution of sodium chloride was replaced with a solution of sodium acetate, resulting in the formation of a silver acetate colloid and sodium nitrate, along with the remaining silver nitrate in the solution. Silver acetate is a local antiinfective that is more water soluble than sodium propionate, silver chloride, or silver iodide, but less water soluble than silver lactate.

Example 8

The process of each of Examples 1, 2, 3, 4, 5, 6, and 7 was repeated, except that the salt solution was added in an amount sufficient to react with 75% of the $AgNO_3$.

Example 9

The process of each of Examples 1, 2, 3, 4, 5, 6, and 7 was repeated, except that the salt solution was added in an amount sufficient to react with 100% of the $AgNO_3$.

Example 10

The process of each of Examples 1, 2, 3, 4, 5, 6, and 7 was repeated, except that the salt solution was added in an amount sufficient to react with 25% of the $AgNO_3$.

Example 11

The process of Example 1 was repeated, except that the NaCl salt solution was added in an amount sufficient to react with 25% of the silver nitrate. Then a 1.0% solution of sodium iodide was added in an amount sufficient to react with another 25% of the silver nitrate to produce a combination of silver chloride and silver iodide colloids from 50% of the silver nitrate.

Example 12

The process of Example 1 was repeated, except that the NaCl salt solution was added in an amount sufficient to react with 25% of the silver nitrate to produce the poorly soluble silver chloride colloid. Then a 1.0% solution of sodium propionate was added in an amount sufficient to react with another 25% of the silver nitrate to produce the slightly water soluble silver propionate colloid. Next, a 1.0% solution of sodium acetate was added in an amount sufficient to react with another 25% of the silver nitrate to produce the somewhat water soluble silver acetate colloid in combination with the poorly soluble silver chloride colloid and the slightly soluble silver propionate colloid from 75% of the silver nitrate.

Example 13

The process of Example 12 was repeated, except that an additional amount of zinc iodide was added to convert 10% of the remaining silver nitrate to a colloid of silver iodide. This produced a coating containing 15% silver nitrate, 25% of the somewhat soluble silver acetate colloid, 25% of the slightly soluble sodium propionate colloid, 25% of the poorly soluble silver chloride colloid, and 10% of the very poorly soluble silver iodide colloid, along with the soluble sodium nitrate and zinc nitrate salt products.

As shown by the above examples, any combination of additional salts in any combination of different amounts can be used to convert some or all of the soluble oligodynamic metal salts into insoluble colloidal salts within a polymer composition.

Example 14

Somewhat water soluble silver salts, such as silver lactate or silver acetate, can be used alone or in combination with the very soluble silver nitrate to produce other compounds that can have antiseptic activity. For example, silver acetate at a 4:1 molar ratio with zinc chloride produces 50% silver chloride colloid and the zinc acetate counter salt, which is also an antiseptic, and leaves 50% unreactive silver acetate. Similarly, other silver salts can be used alone or in combination to produce multiple counter salts that have antiseptic or other desirable activity.

For example, the process of Example 2 was repeated except that a soluble combination of silver nitrate, silver acetate, and silver lactate was used in place of the 10% silver nitrate solution. When the zinc chloride is added, a colloid of silver chloride is formed in the polymer composition and the soluble counter salts zinc nitrate, zinc acetate, and zinc lactate are produced. The zinc acetate and zinc lactate provide antiseptic activity in addition to the antimicrobial activity of the silver salts. In this example any metal salt other than zinc chloride which produces counter salts with the nitrate, acetate, and lactate that have a desired effect, such as antiseptic or antimicrobial activity, can be used. An example of such a salt is copper chloride.

Different oligodynamic salts have different water solubilities. This allows for tailoring of the composition to provide a specific release profile of the antimicrobial agent(s) from the composition. For example, sodium chloride, zinc iodide, sodium citrate, sodium acetate, and sodium lactate can be added to a coating composition containing silver nitrate to produce a coating which contains the water soluble salts silver nitrate and zinc nitrate, the somewhat water soluble salts silver lactate (67 mg/ml water) and silver acetate (10 mg/ml water), the slightly soluble salt silver citrate (0.3 mg/ml water), the poorly soluble salt silver chloride (0.002 mg/ml water), and the very poorly soluble sale silver iodide (0.00003 mg/ml water). By adjusting the proportions of salts having different solubilities in the composition, the release rate of the active oligodynamic agent(s) can be altered to provide a shorter or longer release profile over time.

For example, the process of Example 1 was repeated, except that in addition to the NaCl salt solution, 1% solutions of zinc iodide, sodium citrate, sodium acetate and sodium lactate were added, each in an amount sufficient to react with 15% of the silver nitrate, to produce colloids of silver chloride, silver iodide, silver citrate, silver acetate, and silver lactate in the final coating composition, along with 25% unreacted silver nitrate, and the silver nitrate and zinc nitrate salt products. The difference in solubility of the different silver salts will produce different and prolonged rates of silver ion release in the coating when exposed to body fluid.

Example 15

To form the coating composition for PVC catheters, a 3.3% solution of a polyether polyurethane-urea block copolymer manufactured by Tyndale Plains-Hunter Ltd. (TPH) was prepared in THF. A 3.3% solution of Polyvinyl chloride (PVC) was then prepared in methylene chloride. The two solutions were then combined in equal amounts to provide a 50/50 ratio by weight of the two polymers in solution. A sufficient quantity of 10% silver nitrate ($AgNO_3$) solution in alcohol was then added to the TPH/PVC polymer solution to produce a final silver concentration of approximately 5%, based on coating solids in the solution. A 1% zinc chloride solution in 75/25 mixture by weight of ethanol/water was added to the coating solution in an amount sufficient to react with 50% of the $AgNO_3$ to produce a colloid of the poorly water soluble salt AgCl from half of the $AgNO_3$. The $ZnCl_2$ solution was added slowly to the polymer solution with stirring, and the solution began to turn cloudy with the formation of the fine colloidal AgCl. The amount of water in the final coating solution was slightly less than about 1% of the total solvent weight. A PVC endotracheal tube was then coated by dipping it into the coating composition, followed by drying using standard methods. The finished coating contained both the water soluble, and therefore fast releasing, $AgNO_3$ and the poorly water soluble, and therefore slow releasing, AgCl.

Finally, it will be understood that the preferred embodiments have been disclosed by way of example, and that other modifications may occur to those skilled in the art without departing from the scope and spirit of the appended claims.

I claim:

1. An article of manufacture comprising a substrate and an antimicrobial polymer coating, wherein the polymer coating comprises one or more polymers and a colloid, wherein the colloid comprises oligodynamic metal compounds, wherein the oligodynamic metal compounds are a plurality of metal salts, a plurality of metal oxides, or a combination of at least one metal salt and at least one metal oxide.

2. The article of claim 1 wherein the article comprises a medical device.

3. The article of claim 2 wherein the medical device comprises a catheter, an endotracheal tube, a tracheostomy tube, a wound drainage device, a wound dressing, a stent, an implant, an intravenous catheter, a medical adhesive, a suture, a shunt, a glove, a condom, a contact lens, a gastrostomy tube, medical tubing, cardiovascular products, heart valves, pacemaker leads, a guidewire, or urine collection devices.

4. The article of claim 2 wherein the medical device is a catheter.

5. The article of claim 1 wherein the polymer comprises one or more hydrophilic polymers that are soluble in water or in an organic solvent containing water, one or more hydrophobic polymers, or a combination of both hydrophilic and hydrophobic polymers.

6. The article of claim 5 wherein the hydrophilic polymer is selected from the group consist of polyurethanes, polyvinylpyrrolidones, polyvinyl alcohols, polyethylene glycols, polypropylene glycols, polyoxyethylenes, polyacrylic acid, polyacrylamide, carboxymethyl cellulose, cellulose, dextrans, polysaccharides, starches, guar, xantham and other gums, collagen, gelatins, biological polymers, and mixtures and copolymers thereof.

7. The article of claim 5 wherein the hydrophobic polymer is selected from the group consisting of polytetrafluoroethylene, polyvinyl chloride, polyvinylacetate, poly(ethylene terephthalate), silicone, polyesters, polyamides, polyureas, styrene-block copolymers, polymethyl methacrylate, polyacrylates, acrylic-butadiene-styrene copolymers, polyethylene, polystyrene, polypropylene, natural and synthetic rubbers, acrylonitrile rubber, and mixtures and copolymers thereof.

8. The article of claim 1 wherein at least one of the oligodynamic metal compounds comprises silver.

9. The article of claim 8 wherein silver is present in a compound selected from the group consisting of silver chloride, silver iodide, silver citrate, silver lactate, silver acetate, silver propionate, silver salicylate, silver bromide, silver ascorbate, silver laurel sulfate, silver phosphate, silver sulfate, silver oxide, silver benzoate, silver carbonate, silver sulfadiazine, silver gluconate, and combinations thereof.

10. The article of claim 1 wherein the oligodynamic metal compounds comprise more than one oligodynamic metal.

11. The article of claim 1 wherein the oligodynamic metal compounds comprise compounds having different solubilities in water.

12. The article of claim 11 wherein the oligodynamic metal compounds comprise silver lactate, silver acetate, silver citrate, silver chloride, and silver iodide.

13. An article of manufacture comprising a composition comprising one or more polymers and a colloid wherein the colloid comprises oligodynamic metal compounds, wherein the oligodynamic metal compounds are a plurality of metal salts, a plurality of metal oxides, or a combination of at least one metal salt and at least one metal oxide.

14. A method for the manufacture of an article comprising applying a coating composition to a substrate by spraying the coating composition onto the substrate or by dipping the substrate into the coating composition, wherein the coating composition comprises polymers, monomers, or any combination thereof, and a colloid, wherein the colloid comprises oligodynamic metal compounds, wherein the oligodynamic metal compounds are a plurality of metal salts, a plurality of metal oxides, or a combination of at least one salt and at least one metal oxide.

15. A method comprising the steps of:
 1) forming a composition that comprises a solution, dispersion, or combination thereof of one or more polymers containing a colloid wherein the colloid comprises oligodynamic metal compounds, wherein the oligodynamic metal compounds are a plurality of metal salts, a plurality of metal oxides, or a combination of at least one metal salt and at least one metal oxide, and
 2) drying the composition.

16. The method of claim 15, further comprising processing the dried composition with the application of heat.

17. A method comprising:
 1) forming a composition that comprises a solution, dispersion, or combination thereof of one or more polymers containing a colloid wherein the colloid comprises oligodynamic metal compounds, wherein the oligodynamic metal compounds are a plurality of metal salts, a plurality of metal oxides, or a combination of at least one metal salt and at least one metal oxide;
 2) compounding the composition formed in (1) with one or more polymers; and
 3) processing the composition formed in (2) with the application of heat.

18. A method for the manufacture of an article comprising dipping a form in a composition comprising polymers, monomers, or any combination thereof, and a colloid comprising oligodynamic metal compounds, wherein the oligodynamic metal compounds are a plurality of metal salts, a plurality of metal oxides, or a combination of at least one metal salt and at least one metal oxide.

19. A method for the manufacture of an article comprising casting a composition comprising polymers, monomer, or any combination thereof, and a colloid comprising oligodynamic metal compounds, wherein the oligodynamic metal compounds are a plurality of metal salts, a plurality of metal oxides, or a combination of at least one metal salt and at least one metal oxide.

20. The article of claim 1, wherein the coating is located on one or more exposed surfaces of the articles.

21. The article of claim 1, wherein the article will release at lease some oligodynamic metal into aqueous fluids that come into contact with an exposed surface of the article.

22. An article of manufacture comprising a substrate and an antimicrobial polymer coating located on one or more exposed surfaces of the article, wherein:
 the polymer coating comprises one or more polymers and a colloid, wherein the colloid comprises one or more oligodynamic metal compounds, wherein the oligodynamic metal compounds are at least one metal salt, at least one metal oxide, or a combination of at least one metal salt and at least one metal oxide; and
 the article comprises a medical device.

23. The article of claim 22 wherein the article will release at least some oligodynamic metal into aqueous fluids that come into contact with an exposed surface of the article.

24. The article of claim 22 wherein the article comprises a catheter, an endotracheal tube, a tracheostomy tube, a wound drainage device, a wound dressing, a stent, an implant, an intravenous catheter, a medical adhesive, a suture, a shunt, a glove, a condom, a contact lens, a gastrostomy tube, medical tubing, cardiovascular products, a heart valve, a pacemaker lead, a guidewire, or urine collection devices.

25. The article of claim 22 wherein the article is a catheter.

26. The article of claim 22 wherein the polymer comprises one or more hydrophilic polymers that are soluble in water or in an organic solvent containing water, one or more hydrophobic polymers, or a combination of both hydrophilic and hydrophobic polymers.

27. The article of claim 26 wherein the hydrophilic polymer is selected from the group consisting of polyurethanes, polyvinylpyrrolidones, polyvinyl alcohols, polyethylene glycols, polypropylene glycols, polyoxyethylenes, polyacrylic acid, polyacrylamide, carboxymethyl cellulose, cellulose, dextrans, polysaccharides, starches, guar, xantham and other gums, collagen, gelatins, biological polymers, and mixtures and copolymers therof.

28. The article of claim 26 wherein the hydrophobic polymer is selected from the group consisting of polytetrafluoroethylene, polyvinyl chloride, polyvinlacetate, poly(ethylene terephthalate), silicone, polyesters, polyamides, polyureas, strene-block copolymers, polymethyl methacrylate, polyacrylates, acrylic-butadiene-styrene copolymers, polyethylene, polystrene, polypropylene, natural and synthetic rubbers, acrylonitrile rubber, and mixtures and copolymers thereof.

29. The article of claim 22 wherein at least one of the oligodynamic metal compounds comprises silver.

30. The article of claim 29 wherein silver is present in a compound selected from the group consisting of silver chloride, silver iodide, silver citrate, silver lactate, silver acetate, silver propionate, silver salicylate, silver bromide, silver ascorbate, silver laurel sulfate, silver phosphate, silver sulfate, silver oxide, silver benzoate, silver carbonate, silver sulfadiazine, silver gluconate, and combinations thereof.

31. The article of claim 22 wherein the oligodynamic metal compounds comprise more than one oligodynamic metal.

32. The article of claim 22 wherein the oligodynamic metal compounds comprise compounds having different solubilities in water.

33. The article of claim 32 wherein the oligodynamic metal compounds comprise silver lactate, silver acetate, silver citrate, silver chloride, and silver iodide.

34. A method for the manufacture of an article comprising:
applying a coating composition to a substrate by spraying the coating composition onto the substrate or by dipping the substrate into the coating composition wherein the coating composition comprises polymers, monomers, or any combination thereof, and a colloid, wherein the colloid comprises one or more oligodynamic metal compounds, wherein the oligodynamic metal compounds are at least one metal salt, at least one metal oxide, or a combination of at least one metal salt and at least one metal oxide; and,
allowing the coating composition to form a covering on an exposed surface of the substrate;
wherein the article comprises a medical device.

35. A method comprising the steps of:
1) forming a composition that comprises a solution, dispersion, or combination thereof of one or more polymers containing a colloid wherein the colloid comprises one or more oligodynamic metal compounds, wherein the one or more oligodynamic metal compounds are at least one metal salt, at least one metal oxide, or a combination of at least one metal salt and at least one metal oxide; and
2) drying the composition;
wherein the method results in formation of a medical device comprising the composition located on at least one exposed surface.

36. The method of claim 35, further comprising processing the dried composition with the application of heat.

37. A method for the manufacture of an article comprising:
1) forming a composition that comprises a solution, dispersion, or a combination thereof of one or more polymers containing a colloid wherein the colloid comprises one or more oligodynamic metal compounds, wherein the oligodynamic metal compounds are at least one metal salt, at least one metal oxide, or a combination of at least one metal salt and at least one metal oxide;
2) compounding the composition formed in (1) with one or more polymers; and
3) processing the composition formed in (2) with the application of heat;
wherein the article comprises a medical device and the composition formed in step (2) is located on at least one exposed surface of the article.

38. A method for the manufacture of an article comprising dipping a form in a composition comprising polymers, monomers, or any combination thereof and a colloid comprising one or more oligodynamic metal compounds, wherein:
the oligodynamic metal compounds are at least one metal salt, at least one metal oxide, or a combination of at least one metal salt and at least one metal oxide;
the composition is located on at least one exposed surface of the article; and,
the article comprises a medical device.

39. A method for the manufacture of an article comprising casting a composition comprising polymers, monomers, or any combination thereof, and a colloid comprising one or more oligodynamic metal compounds, wherein:
the oligodynamic metal compounds are at least one metal salt, at least one metal oxide, or a combination of at least one metal salt and at least one metal oxide;
the composition is located on at least one exposed surface of the article; and,
the article comprises a medical device.

40. An article of manufacture comprising a substrate and an antimicrobial polymer coating located on one or more exposed surfaces of the article, wherein:
the polymer coating comprises a polyvinyl chloride, a polyurethane-urea block copolymer and a colloid;
the substrate comprises a polyvinyl chloride;
the colloid comprises silver chloride; and
the article comprises an endotracheal tube.

41. An article of manufacture comprising a substrate and an antimicrobial polymer coating located on one or more exposed surfaces of the article, wherein:
the polymer coating comprises a polyurethane-urea block copolymer, silver nitrate, and a colloid;
the substrate comprises latex;
the colloid comprises silver chloride; and
the article comprises a Foley catheter.

42. An article of manufacture comprising a composition comprising one or more polymers and a colloid wherein the colloid comprises one or more oligodynamic metal compounds, wherein:
the oligodynamic metal compounds are at least one metal salt, at least one metal oxide, or a combination of at least one metal salt and at least one metal oxide;
at least some of the composition is located at an exposed surface of the article; and
the article comprises a medical device.

43. An article of manufacture comprising a substrate and an antimicrobial polymer coating located one one or more exposed surfaces of the article, wherein:

the polymer coating comprises one or more polymers and a colloid, wherein the colloid comprises one or more oligodynamic metal salts; and the article comprises a medical device.

44. An article of manufacture comprising a substrate and an antimicrobial polymer coating, wherein the polymer coating comprises one or more polymers and a colloid, wherein the colloid comprises a plurality of oligodynamic metal salts.

45. An article of manufacture comprising a composition comprising one or more polymers and a colloid wherein the colloid comprises a plurality of oligodynamic metal salts.

46. An article of manufacture comprising a composition comprising one or more polymers and a colloid wherein the colloid comprises one or more oligodynamic metal salts, wherein:

at least some of the composition is located at an exposed surface of the article; and the article comprises a medical device.

47. A method for the manufacture of an article comprising applying a coating composition to a substrate by spraying the coating composition onto the substrate or by dipping the substrate into the coating composition, wherein the coating composition comprises polymers, monomers, or any combination thereof, and a colloid, wherein the colloid comprises a plurality of oligodynamic metal salts.

48. A method for the manufacture of an article comprising:

applying a coating composition to a substrate by spraying the coating composition onto the substrate or by dipping the substrate into the coating composition wherein the coating composition comprises polymers, monomers, or any combination thereof, and a colloid, wherein the colloid comprises at least one oligodynamic metal salt; and, allowing the coating composition to form a covering on an exposed surface of the substrate;

wherein the article comprises a medical device.

* * * * *

US006716895C1

(12) EX PARTE REEXAMINATION CERTIFICATE (7877th)
United States Patent
Terry

(10) Number: US 6,716,895 C1
(45) Certificate Issued: Nov. 16, 2010

(54) POLYMER COMPOSITIONS CONTAINING COLLOIDS OF SILVER SALTS

(75) Inventor: Richard N. Terry, Conyers, GA (US)

(73) Assignee: C.R. Bard, Inc., Murray Hill, NJ (US)

Reexamination Request:
No. 90/010,714, Oct. 13, 2009

Reexamination Certificate for:
Patent No.: 6,716,895
Issued: Apr. 6, 2004
Appl. No.: 09/461,846
Filed: Dec. 15, 1999

(51) Int. Cl.
*A61L 31/14* (2006.01)
*A61L 17/00* (2006.01)
*A61L 15/16* (2006.01)
*A61L 24/00* (2006.01)
*A61L 27/00* (2006.01)
*A61L 27/34* (2006.01)
*A61L 27/54* (2006.01)
*A61L 29/00* (2006.01)
*A61L 29/08* (2006.01)
*A61L 29/16* (2006.01)
*A61L 31/00* (2006.01)
*A61L 31/10* (2006.01)
*A61L 31/16* (2006.01)
*A61L 31/08* (2006.01)
*A01N 25/10* (2006.01)
*A01N 59/16* (2006.01)
*A01N 59/20* (2006.01)
*C09D 5/14* (2006.01)
*C09D 201/00* (2006.01)

(52) U.S. Cl. .................. 523/122; 524/403; 604/264; 604/265; 604/905

(58) Field of Classification Search ............. 523/122
See application file for complete search history.

(56) References Cited

U.S. PATENT DOCUMENTS

| | | |
|---|---|---|
| 3,699,956 A | 10/1972 | Kitrilakis et al. |
| 3,975,350 A | 8/1976 | Hudgin et al. |
| 4,054,139 A | 10/1977 | Crossley |
| 4,145,370 A | 3/1979 | Sreeves et al. |
| 4,156,066 A | 5/1979 | Gould |
| 4,156,067 A | 5/1979 | Gould |
| 4,255,550 A | 3/1981 | Gould |
| 4,256,067 A | 3/1981 | Fukui |
| 4,284,444 A | 8/1981 | Bernstein et al. |
| 4,359,558 A | 11/1982 | Gould et al. |
| 4,508,889 A | 4/1985 | Noren et al. |
| 4,603,152 A | 7/1986 | Laurin et al. |
| 4,642,267 A | 2/1987 | Creasy et al. |
| 4,645,816 A | 2/1987 | Pohl et al. |
| 4,729,914 A | 3/1988 | Kliment et al. |
| 4,789,720 A | 12/1988 | Teffenhart |
| 4,810,543 A | 3/1989 | Gould et al. |
| 4,963,310 A | 10/1990 | Mitamura et al. |
| 5,061,424 A | 10/1991 | Karimi et al. |
| 5,173,531 A | 12/1992 | Kissel |
| 5,227,434 A | 7/1993 | Katz |
| 5,344,712 A | 9/1994 | Basil et al. |
| 5,476,509 A | 12/1995 | Keogh et al. |
| 5,573,783 A | 11/1996 | Desieno et al. |
| 5,728,781 A | 3/1998 | Usuki et al. |
| 5,736,032 A | 4/1998 | Cox et al. |
| 5,788,687 A | 8/1998 | Batich et al. |
| 5,798,115 A | 8/1998 | Santerre et al. |
| 5,928,174 A | 7/1999 | Gibbins |
| 5,945,032 A | 8/1999 | Breitenbach et al. |
| 5,976,562 A | 11/1999 | Krall et al. |
| 6,063,849 A | 5/2000 | Morris et al. |
| 6,106,853 A | 8/2000 | Cox et al. |
| 6,150,004 A | 11/2000 | Oikawa et al. |
| 6,296,863 B1 | 10/2001 | Trogolo et al. |
| 6,329,488 B1 | 12/2001 | Terry et al. |
| 6,355,858 B1 | 3/2002 | Gibbins |
| 6,399,689 B1 | 6/2002 | Scarlette |
| 6,478,861 B1 | 11/2002 | Kwan et al. |
| 6,579,539 B2 | 6/2003 | Lawson et al. |
| 6,596,401 B1 | 7/2003 | Terry et al. |
| 6,605,751 B1 | 8/2003 | Gibbins et al. |
| 6,669,981 B2 | 12/2003 | Parsons et al. |
| 6,756,124 B2 | 6/2004 | Kanamori et al. |
| 6,908,681 B2 | 6/2005 | Terry et al. |
| 6,949,598 B2 | 9/2005 | Terry |
| 7,029,755 B2 | 4/2006 | Terry et al. |
| 7,087,249 B2 | 8/2006 | Burrell et al. |
| 7,179,849 B2 | 2/2007 | Terry |
| 7,378,156 B2 | 5/2008 | Terry |

(Continued)

FOREIGN PATENT DOCUMENTS

| | | |
|---|---|---|
| CA | 2278706 | 7/1998 |
| WO | 92/11877 A1 | 7/1992 |
| WO | 97/31709 A1 | 9/1997 |
| WO | 00/30697 A1 | 6/2000 |
| WO | 01/43788 A2 | 6/2001 |
| WO | 01/53414 A1 | 7/2001 |
| WO | 02/18003 A1 | 3/2002 |
| WO | 2007/130734 A2 | 11/2007 |

OTHER PUBLICATIONS colloid. (n.d.) Dorland's Medical Dictionary for Health Consumers. (2007). Retrieved Mar. 22, 2010 from http://medical–dictionary.thefreedictionary.com/colloid.*

(Continued)

*Primary Examiner*—Bruce Campell

(57) ABSTRACT

The present invention relates to antimicrobial compositions, methods for the production of these compositions, and use of these compositions with medical devices, such as catheters, and implants. The compositions of the present invention advantageously provide varying release kinetics for the active ions in the compositions due to the different water solubilities of the ions, allowing antimicrobial release profiles to be tailored for a given application and providing for sustained antimicrobial activity over time. More particularly, the invention relates to polymer compositions containing colloids comprised of salts of one or more oligodynamic metal, such as silver. The process of the invention includes mixing a solution of one or more oligodynamic metal salts with a polymer solution or dispersion and precipitating a colloid of the salts by addition of other salts to the solution which react with some or all of the first metal salts. The compositions can be incorporated into articles or can be employed as a coating on articles such as medical devices.

U.S. PATENT DOCUMENTS

| | | | |
|---|---|---|---|
| 2003/0007985 | A1 | 1/2003 | Chevalier et al. |
| 2003/0049300 | A1 | 3/2003 | Terry et al. |
| 2005/0064176 | A1 | 3/2005 | Terry |
| 2008/0199536 | A1 | 8/2008 | Terry |
| 2008/0199623 | A1 | 8/2008 | Terry |

OTHER PUBLICATIONS

Baselski et al. "The Standardization of Criteria for Processing and Interpreting Laboratory Specimens in Patients with Suspected Ventilator–Associated Pneumonia." *Chest* 1992; 102[Supp]: 571S–579S.

Baron et al. "Classification and Identification of Bacteria." In: Murrary P R, ed. Manual of Clinical Microbiology. Washington, D.C.: ASM Press, 1995; 249–264.

Marquette et al. "Characterization of an Animal Model of Ventilator–Acquired Pneumonia." *Chest* 1999; 115: 200–209.

Laperuta et al., "Preparation and Characterization of Silver Colloid/Polymer Composite Nonlinear Optical Materials," Department of Chemistry, SPIE1497, p. 357–366(1991).

Olson et al., "Silver–Coated Endotracheal Tubes Associated with Reduced Bacterial Burden in the Lungs of Mechanically Ventilated Dogs," *Respiratory and Critical Care Medicine,* vol. 163, No. 5, p. A754 (2001).

Olson et al., "Silver–Coated Endotracheal Tubes Associated with Reduced Bacterial Burden in the Lungs of Mechanically Ventilated Dogs," *Laboratory and Animal Investigations,* vol. 121, No. 3, p. 863–870 (2002).

International Search Report issued in connection with PCT/US00/42372 on Sep. 11, 2001.

International Preliminary Examination Report issued on connection with PCT/US00/42372, completed Apr. 10, 2002.

European Examination Report issued in connection with EP 03 003 119.9, dated Apr. 27, 2006.

EP Official Communication issued in connection with EP 02 804 480.8, dated Oct. 29, 2007.

EP Official Action issued in connection with EP 00 992 538.9, mailed Feb. 3, 2009.

Callister, William D., Jr., *Materials Science and Engineering: An Introduction, 4th Edition,* New York: John Wiley & Sons, Inc., 1997, p. 477.

Stevens, Malcolm P., *Polymer Chemistry: An Introduction, 3rd Edition,* New York: Oxford University Press, 1999, p. 85–86 and 537.

Rogers, Martin E., and Long, Timothy E. (editors), *Synthetic Methods in Step–Growth Polymers,* New Jersey: John Wiley & Sons, Inc., 2003, p. 197.

"colloid." *The American Heritage® Dictionary of the English Language, Third Edition.* Houghton Mifflin Company, 1997.

Oxtoby and Nachtrieb, *Principles of Modern Chemistry, 3rd Edition,* Saunders College Publishing, 1996, p. 164 and 253.

Kroschwitz, Jacqueline I. (editor), *Concise Encyclopedia of Polymer Science and Engineering,* John Wiley & Sons, Inc., 1990, p. 109–110 and 186.

Berg, Jeremy M., Tymoczko, John L., and Stryer, Lubert, *Biochemistry: 6th Edition,* New York: W.H. Freeman and Company, 2007, p. 46–49.

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-26, 29-34, 36-38, 40 ,41, 44, 45, 47 and 48 is confirmed.

Claims 27, 28, 35, 39, 42, 43 and 46 are determined to be patentable as amended.

27. The article of claim 26 wherein the hydrophilic polymer is selected from the group consisting of polyurethanes, polyvinylpyrrolidones, polyvinyl alcohols, polyethylene glycols, polypropylene glycols, polyoxyethylenes, polyacrylic acid, polyacrylamide, carboxymethyl cellulose, cellulose, dextrans, polysaccharides, starches, guar, xantham and other gums, collagen, gelatins, biological polymers, and mixtures and copolymers [therof] *thereof*.

28. The article of claim 26 wherein the hydrophobic polymer is selected from the group consisting of polytetrafluoroethylene, polyvinyl chloride, [polyvinlacetate] *polyvinylacetate*, poly(ethylene terephthalate), silicone, polyesters, polyamides, polyureas, [strene-block] *styrene-block* copolymers, polymethyl methacrylate, polyacrylates, acrylic-butadiene-styrene copolymers, polyethylene, [polystrene] *polystyrene*, polypropylene, natural and synthetic rubbers, acrylonitrile rubber, and mixtures and copolymers thereof.

35. A method comprising the steps of:
1) forming a composition that comprises a solution, dispersion, or combination thereof of one or more polymers containing a colloid wherein the colloid comprises one or more oligodynamic metal compounds, wherein the one or more oligodynamic metal compounds are at least one metal salt, at least one metal oxide, or a combination of at least one metal salt and at least one metal oxide; and
2) drying the composition; wherein the method results in formation of a *coated* medical device comprising the composition [located] *coated* on at least one exposed surface.

39. A method for the manufacture of an article comprising casting a composition comprising polymers, monomers, or any combination thereof, and a colloid comprising one or more oligodynamic metal compounds, wherein:
the oligodynamic metal compounds are at least one metal salt, at least one metal oxide, or a combination of at least one metal salt and at least one metal oxide; the composition is [located] *in the form of a coating, and the coating is coated* on at least one exposed surface of the article; and,
the article comprises a medical device.

42. An article of manufacture comprising a composition comprising one or more polymers and a colloid wherein the colloid comprises one or more oligodynamic metal compounds, wherein:
the oligodynamic metal compounds are at least one metal salt, at least one metal oxide, or a combination of at least one metal salt and at least one metal oxide;
[at least some of] the composition *is in the form of a coating, and the coating* is located at an exposed surface of the article; and the article comprises a medical device.

43. An article of manufacture comprising a substrate and an antimicrobial polymer coating located [one] *on* one or more exposed surfaces of the article, wherein: the polymer coating comprises one or more polymers and a colloid, wherein the colloid comprises one or more oligodynamic metal salts; and the article comprises a medical device.

46. An article of manufacture comprising a *coating having a* composition comprising one or more polymers and a colloid wherein the colloid comprises one or more oligodynamic metal salts, wherein:
at least some of the composition is [located at an] *coated on an* exposed surface of the article; and
the article comprises a medical device.

* * * * *